United States Patent [19]
Hagedorn et al.

[11] Patent Number: 5,998,628
[45] Date of Patent: Dec. 7, 1999

[54] NON-EXPLOSIVE PREPARATIONS OF 1-HYDROXYBENZOTRIAZOLE

[75] Inventors: Ferdinand Hagedorn; Helmut Fiege, both of Leverkusen, Germany

[73] Assignee: Bayer Aktiengesellschaft, Leverkusen, Germany

[21] Appl. No.: 09/043,356

[22] PCT Filed: Sep. 10, 1996

[86] PCT No.: PCT/EP96/03958

§ 371 Date: Mar. 16, 1998

§ 102(e) Date: Mar. 16, 1998

[87] PCT Pub. No.: WO97/11062

PCT Pub. Date: Mar. 27, 1997

[30] Foreign Application Priority Data

Sep. 22, 1995 [DE] Germany .......................... 195 35 245

[51] Int. Cl.⁶ ............................................... C07D 249/18
[52] U.S. Cl. ............................................................ 548/259
[58] Field of Search ............................................. 548/259

[56] References Cited

U.S. PATENT DOCUMENTS

| | | | |
|---|---|---|---|
| 3,725,380 | 4/1973 | König et al. ................... | 260/112.5 |
| 3,895,170 | 7/1975 | Tanaka et al. ................... | 428/457 |

FOREIGN PATENT DOCUMENTS

| | | |
|---|---|---|
| 0064714 | 11/1982 | European Pat. Off. . |
| 2455623 | 5/1976 | Germany . |
| 3117985 A1 | 11/1982 | Germany . |
| 3406011 A1 | 8/1985 | Germany . |
| 1242954 | 8/1971 | United Kingdom . |

OTHER PUBLICATIONS

Cram and Hammond, "Organic Chemistry", McGraw Hill Book Co., NY (1964) 2nd Ed. pp. 565–567.
Derwent Abstract of JP–A–01 039 009 (Feb. 9, 1989).
Schmidt et al., "2–Trifluoracetylthiopyridine 1–Hydroxy-benzotriazole: A Powerful Reagent for Peptide Synthesis" J. Chem. Soc. Commun. (1993) pp. 1461–1462.
Chemical Abstracts, vol. 120 (1994) p. 1114, CAS: 120 Abstract No. 135115h (Abstract of IDS Ref. AI, Schmidt et al.).
Chemical Abstracts, vol. 122 (1996) p. 1116, CAS: 122 Abstract No. 106468m, (abstract of IDS Ref. AL, Sivanadaiah et al.).
Sivanadaiah et al., "Synthesis of peptides mediated by KOBt" International Journal of Peptide & Protein Research, vol. 44 (1994) pp. 24–30.
28–Heterocycles, vol. 94 (1981) p. 767 CAS: 94 Abstract No. 139818g Abstract of JP–A–55 151 576.
General Chemistry, p. 3 Abstract of JP–A–55 151 576 Abstract No. 06747 (1980).
28–Heterocycles, vol. 93, (1980) CAS: 94 Abstract No. 46683y Abstract of JP–A–54160 378.
Metallurgy, Week C05, p. 11, Abstract of JP A–54 160 378, Abstract No. 08398C/05.

*Primary Examiner*—Patricia L. Morris
*Attorney, Agent, or Firm*—Sprung Kramer Schaefer & Briscoe

[57] ABSTRACT

Preparations consisting of 5 to 90%, relative to the total weight of the preparations, of mainly neutralized 1-hydroxy-benzotriazole of the formula

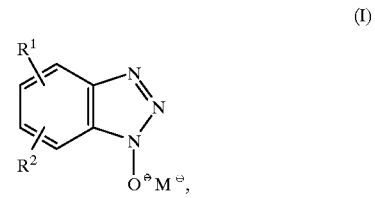

(I)

in which

R¹ and R², independently of one another, represent hydrogen or methyl and

M⊕ is one equivalent of an alkali metal or alkaline earth metal cation or H⊕, whereby M⊕ is present in the range of 85-100 equivalent-% as alkali metal or alkaline earth metal cation and in the range of 15-0 equivalent-% as H⊕, and the remainder to 100% of water, whereby the water containing preparations have a pH value of from 3 to 11 are nonexplosive and can be handled without danger.

For the preparation, unsubstituted 1-hydroxy-benzotriazole is neutralized with an aqueous solution or suspension of a hydroxide, bicarbonate or carbonate of an alkali metal or alkaline earth metal. These preparations may be present as solutions, suspensions or pastes.

8 Claims, No Drawings

NON-EXPLOSIVE PREPARATIONS OF 1-HYDROXYBENZOTRIAZOLE

The present invention relates to nonexplosive preparations of 1-hydroxy-benzotriazole which consist of neutralized 1-hydroxy-benzotriazole and water. They are prepared by reaction of unneutralized 1-hydroxy-benzotriazole with hydroxides, bicarbonates or carbonates of alkali metals or alkaline earth metals to the neutral point in aqueous solution. The preparations according to the invention may be present as a solution, suspension or paste, depending on the solubility of the neutralized 1-hydroxy-benzotriazoles and on the temperature. The preparations according to the invention do not constitute an explosion hazard in the meaning of the law of the Federal German Republic on substances constituting an explosion hazard, of 17.04.1986 (Bundesgesetzblatt [Federal Law Gazette] page 577).

1-Hydroxy-benzotriazole is used for reducing the racemization in peptide syntheses, in particular in syntheses by the dicyclohexyl-carbodiimide or the active ester method. Furthermore, it serves as particularly effective mediator substance in an enzymatic bleaching process by atmospheric oxidation in the paper and pulp industry. In the same manner as the unsubstituted parent substance, methyl-substituted 1-hydroxy-benzotriazoles, for example 1-hydroxy-4-methyl-benzotriazole or 1-hydroxy-5-methyl-benzotriazole or mixtures of the two compounds, are also suitable for this purpose. The preparations according to the invention are suitable for these purposes, both in the unneutralized form obtainable again by acidification or directly in the form of the preparations according to the invention, in which the 1-hydroxy-benzotriazoles are present in the form of their alkali metal or alkaline earth metal salts. The explosion-proof nature of the preparations according to the invention plays an important role in the storage, the transport and the handling of the stated substances.

It is known that 1-hydroxy-benzotriazoles are substances which constitute an extreme explosion hazard. Particularly during drying, milling, sieving or during, heating or on contact with ignition sources or hot surfaces, there are therefore risks of accidents due to spontaneous decomposition reactions. Accordingly, the handling of such substances is subject to particular regulations. The use of pure 1-hydroxy-benzotriazoles in practice is thus greatly restricted or even made impossible by their thermal and mechanical sensitivity.

There has been no lack of effort to eliminate or at least to reduce the explosion hazard of 1-hydroxy-benzotriazoles by additives, so-called desensitizers. The addition of water alone is not sufficient here. The reduction or a limited elimination of the explosion hazard was achieved by mixing with fine-particled solids (DE-OS (German Published Specification) 31 17 985). However, the range of use of such mixtures is restricted in an often undesired manner by the additives. In addition, especially the careful mixing and the necessity of the fine-particled nature of the additives require a certain effort, which is expensive and moreover does not eliminate tile flammability of the mixture in most cases.

In detailed investigations of behavior of, for example, sodium 1-hydroxy-benzotriazole towards thermal and mechanical stress, it was found that dried, anhydrous 1-hydroxy-benzotriazole sodium salt is likewise thermally sensitive and impact-sensitive but not sensitive to friction. Further investigations have finally shown that preparations of the alkali metal or alkaline earth metal salts of 1-hydroxy-benzotriazole with water are to be regarded as constituting neither a thermal nor a mechanical explosion hazard. Forms of 1-hydroxy-benzotriazole which can be handled without danger are thus provided.

The invention relates to nonexplosive preparations of 1-hydroxy-benzotriazole, consisting of 5 to 90%, relative to the total weight of the preparations, of mainly neutralized 1-hydroxy-benzotriazole of the formula

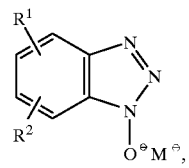

(I)

in which

R$^1$ and R$^2$, independently of one another, represent hydrogen or methyl and

M$^{\oplus}$ is one equivalent of an alkali metal or alkaline earth metal cation or H$^{\oplus}$ whereby M$^{\oplus}$ is present in the range of 85-100 equivalent-% as alkali metal or alkaline earth metal cation and in the range of 15-0 equivalent-% as H$^{\oplus}$, and the remainder to 100% of water, whereby the water containing preparations have a pH value of from 3 to 11.

In preferred preparations, R$^2$ is hydrogen; in particular preferred preparations, R$^1$ and R$^2$ are hydrogen.

In further preferred preparations, M$^{\oplus}$ represents Na$^{\oplus}$, K$^{\oplus}$, ½ Mg$^{\oplus\oplus}$ or ½ Ca$^{\oplus\oplus}$. In particularly preferred further preparations, M$^{\oplus}$ represents Na$^{\oplus}$ or K$^{\oplus}$.

It is further allowable to not carry out the neutralization completely up to the equivalence point. Thus, it is possible according to the invention, to have M$^{\oplus}$ present in a meaning as an alkali metal or alkaline earth metal cation down to 85 equivalent-%, preferably to 90, especially preferably to 98 equivalent-% while the remainder of up to 100 equivalent-%, namely 15-0, preferably 10-0, especially preferably 2-0 equivalent-% means H$^{\oplus}$. However, it is just so possible to permit alkali metal or alkaline earth metal cations in an amount slightly above the equivalence point. The pH value of the water containing preparations according to the invention may therefore be in the range of 5–8.

Further preferred preparations consist of 20 to 70%, relative to their total weight, of mainly neutralized 1-hydroxy-benzotriazole of the above formula (I). Owing to the considerable water solubility, for example of the sodium or potassium salt of the above formula (I), clear aqueous solutions containing up to 60 to 65% by weight of salt of the formula (I) can be prepared in both cases. With regard to their use, such solutions have the advantage of good meterability compared with the crystalline 1-hydroxy-benzotriazole which constitutes an explosion hazard. In particular, the potassium salt solutions furthermore possess the advantage of still having no tendency to crystallize on cooling to close to 0° C. On the other hand, by often only slight cooling, such solutions or the suspensions formed therefrom when the solubility is exceeded and having industrially interesting concentrations of alkali metal or alkaline earth metal salt can be brought into a quasi-solid, water-containing form which is comparable with a paste. It may be assumed that the salt of the formula (I) is surrounded therein by a very bulky hydrate envelope. Thus, for example, a sodium 1-hydroxy-benzotriazole solution which is about 45% strength by weight and has been prepared at 40° C. can be converted into the solidified solid form of a water-containing paste by cooling to room temperature.

This form can be advantageous, for example, with respect to storage and transportation. This solidified solution can be converted back into the liquid form with only very small energy consumption, for example by slight heating. Where unneutralized 1-hydroxy-benzotriazole is required, this unneutralized form can be recovered from the preparations according to the invention by acidification.

It has thus been possible to offer, for all applications of 1-hydroxy-benzotriazole and its salts, preparations in the liquid, liquid/solid or quasi-solid state (solutions, suspensions, pastes) which are safe to handle.

According to the invention, the preparation of the preparations according to the invention is effected after the preparation of the 1-hydroxy-benzotriazoles by neutralization with an aqueous solution or suspension of alkali metal or alkaline earth metal hydroxide, alkali metal or alkaline earth metal bicarbonate or alkali metal or alkaline earth metal carbonate at 0 to 100° C., preferably at 15 to 60° C. In a preferred procedure, a water-moist unneutralized 1-hydroxy-benzotriazole is used. It is thus not necessary for a 1-hydroxy-benzotriazole obtained in water-moist form from the preparation to be dried in a dangerous manner.

The 1-hydroxy-benzotriazole required for the preparation of the preparations according to the invention can be prepared, for example in a manner known in principle, from o-nitrochlorobenzene with hydrazine hydrate and with subsequent reaction with sodium hydroxide solution; the solution obtained here is acidified and the 1-hydroxy-benzotriazole precipitated is neutralized, according to the invention, into the preparations described, after filtration and dissolving away of salt residues. Here, it is possible both to introduce the 1-hydroxy-benzotriazole into initially taken dissolved or suspended alkaline alkali metal or alkaline earth metal compound of the type described and to proceed in the converse manner. In both cases, the reaction is carried out up to the above given equivalent percentages and up to the above given pH figures, which can be monitored by known methods, such as, for example, by titration electrodes.

For the preparation of preparations according to the invention having a content of up to 90%, relative to the total weight of the preparations, of mainly neutralized 1-hydroxy-benzotriazole of the formula (I), water can be distilled off from more dilute solutions or suspensions in the usual manner known to a person skilled in the art, for example in vacuo.

In a further process for the preparation of the 1-hydroxy-benzotriazoles required according to the invention, it is also possible for nitrobenzene which are poly-substituted by chlorine and in which at least one chlorine atom is in the o position relative to the nitro group to first be reacted with hydrazine hydrate and alkali metal hydroxide to give an aqueous solution of a chlorine-substituted 1-hydroxy-benzotriazole; this solution can then be catalytically dehalogenated under hydrogenating conditions, for example in a one-pot reaction, and gives the 1-hydroxy-benzotriazole after acidification, filtration and washing out of salt residues in the manner described above and can likewise be converted into the nonexplosive preparations according to the invention in the manner described above.

EXAMPLES

Example 1

150 g of hiydrazine hydrate and 106.5 g of sodium carbonate (99.5% strength) were initially taken in a stirred flask and heated to about 90° C. In the course of 70 min, 175.5 g of molten o-nitrobenzene were added dropwise. Thereafter, the mixture was stirred 4.5 hours at 100° C. and for a further 2 hours at 105° C. After the addition of 350 ml of water, a clear solution was obtained and was stirred tlioroughly with two portions each of 150 ml of toluene. Residual toluene was removed by partial distillation of the aqueous phase, and the aqueous phase was acidified with 260 ml of concentrated hydrochloric acid to pH 1. The mixture containing the precipitated 1-hydroxy-benzotriazole was cooled to 5° C., filtered off with suction and washed chloride-free with water. The yield was 90.1% of the theoretical yield. The water-moist 1-hydroxy-benzotriazole (0.89 mol) was dissolved, without drying, in an aqueous sodium hydroxide solution, prepared from 146.1 g of water and 79.4 g of 45% strength sodium hydroxide solution at 40° C. to a pH of 7.05. A clear solution of about 45% strength was obtained. The mixture solidified on cooling to room temperature (about 20° C.), but could readily be converted back into a clear solution again by heating to 40° C.

The preparation obtained was subjected to the so-called steel sleeve test. For this purpose, for testing the thermal sensitivity, 6 samples were heated for a period of 40 to 47 seconds in a steel sleeve of 25 mm diameter, 0.5 mm wall thickness and 75 mm height, which had an openings in the upper cover plate of 1 mm, 2 mm or 6 mm diameter. An explosion did not occur in any case. To test the mechanical sensitivity, samples between 2 steel rams of 10 mm diameter were struck by a drop hammer having a mass of 10 kg. The height of drop was 40 and 100 cm. Of the 6 experiments carried out at both heights of drop, a reaction did not occur in any case. The tested preparation thus does not constitute an explosion hazard in this form in the meaning of the law on substances constituting an explosion hazard, stated in the introduction.

Example 2

165 g of water-moist 1-hydroxy-benzotriazole having a water content of 37.6 g, corresponding to 0.95 mol of 1-hydroxy-benzotriazole, were prepared according to the data of Example 1 and were introduced in portions into an aqueous potassium hydroxide solution, prepared from 62.6 g of potassium hydroxide, 85% strength, and 50 ml of water. A 59% strength clear aqueous solution of potassium salt of 1-hydroxy-benzotriazole was obtained in this manner and showed no crystallization phenomena on cooling and seeding with potassium salt crystals down to −10° C.

In the test for explosion hazard, which was described in Example 1, an explosion occurred in 3 experiments in the measurement of the thermal sensitivity with an opening of 1 mm diameter; with openings of 2 and 6 mm diameter, no explosions occurred in 3 experiments in each case. In the measurement of the mechanical sensitivity with the drop hammer, no reaction occurred in 6 experiments in each case at both heights of drop of 40 to 100 cm.

Example 3

A mixture of 96 g of 2,5-dichloronitrobenzene and 96 g of 2,3-dichloronitrobenzene, which mixture was melted to a clear melt at 70° C., was added dropwise at 90 to 100° C. to an initially taken solution of 300 g of hydrazine hydrate and 75 g of water while stirring in the course of 75 minutes with gentle cooling. The reaction mixture was then stirred for 3 hours at 100° C. Thereafter, 177.6 g of 45% strength sodium hydroxide solution were added dropwise. The excess hydrazine was distilled off in the presence of n-heptanol with steam. After removal of the n-heptanol with steam, a salt solution was obtained and was mixed with 1 mol of 45% strength sodium hydroxide solution in a steel autoclave and dehalogenated in the presence of 10 g of a 5% strength palladium/carbon catalyst (moist) at 60° C. with hydrogen at 5 bar (duration: about 1 hour). After the catalyst had been separated off, the solution was acidified to pH 1 with hydrochloric acid, and the precipitated 1-hydroxy-benzotriazole (yield: 52.5 g dry, 97% of the theoretical yield) was filtered off with suction, washed chloride-free with water and introduced moist into 86.2 g of 45% strength aqueous sodium hydroxide solution at 40° C. The clear solution obtained at this temperature was cooled to about 20° C. The mixture solidified on seeding.

We claim:

1. Nonexplosive preparation of 1-hydroxy-benzotriazole, consisting of 5 to 90%, relative to the total weight of the preparation, of mainly neutralized 1-hydroxy-benzotriazole of the formula

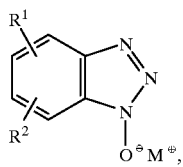

(I)

in which

R$^1$ and R$^2$, independently of one another, represent hydrogen or methyl and

M$^⊕$ is one equivalent of an alkali metal or alkaline earth metal cation or H$^⊕$, whereby M$^⊕$ is present in the range of 85-100 equivalent-% as alkali metal or alkaline metal cation and in the range of 15-0 equivalent-% as H$^⊕$, which has been washed chloride free with water, and the remainder to 100% of water, whereby the water containing preparations have a pH value of from 5 to 8.

2. Preparation according to claim 1, wherein R$^2$ is hydrogen.

3. Preparation according to claim 1, wherein M$^⊕$ represents Na$^⊕$, K$^⊕$, ½ Mg$^{⊕⊕}$ or ½ Ca$^{⊕⊕}$.

4. Preparation according to claim 1, wherein M$^⊕$ is present to 90-100 equivalent-% as alkali metal or alkaline earth metal cation, and to 10-0 equivalent-% as H$^⊕$.

5. Preparation according to claim 1, consisting of 20 to 70%, relative to its weight, of neutralized 1-hydroxy-benzotriazole of the formula (I).

6. Process for the preparation of nonexplosive preparation of 1-hydroxy-benzotriazole, consisting of 5 to 90%, relative to the total weight of the preparation, of mainly neutralized 1-hydroxy-benzotriazole of the formula

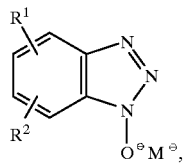

(I)

in which

R$^1$ and R$^2$, independently of one another, represent hydrogen or methyl and

M$^⊕$ is one equivalent of an alkali metal or alkaline earth metal cation or H$^⊕$, whereby M$^⊕$ is present in the range of 85-100 equivalent-% as alkali metal or alkaline metal cation and in the range of 15-0 equivalent-% as H$^⊕$, and the remainder to 100% of water, whereby the water containing preparation has a pH value of from 5 to 8, wherein an unneutralized 1-hydroxy-benzotriazole of the above formula, in which M$^⊕$ is replaced by hydrogen, is first washed chloride-free with water and is then neutralized with an aqueous solution or suspension of alkali metal or alkaline earth metal hydroxides, alkali metal or alkaline earth metal bicarbonates or alkali metal or alkaline earth metal carbonates at 0 to 100° C.

7. Process according to claim 6, wherein a water-moist unneutralized 1-hydroxy-benzotriazole is used.

8. Process according to claim 6, wherein the reaction is carried out at 15 to 60° C.

* * * * *